United States Patent [19]

Grohe et al.

[11] E Patent Number: Re. 32,975

[45] Reissued Date of Patent: Jul. 4, 1989

[54] 4-PYRIDONE-3-CARBOXYLIC ACIDS AND/OR DERIVATIVES THEREOF

[75] Inventors: Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 733,996

[22] Filed: May 14, 1985

Related U.S. Patent Documents

Reissue of:

[64] Patent No.: 4,284,629
Issued: Aug. 18, 1981
Appl. No.: 8,634
Filed: Feb. 1, 1979

[30] Foreign Application Priority Data

Feb. 24, 1978 [DE] Fed. Rep. of Germany ..... 2808070

[51] Int. Cl.[4] ..... C07D 471/00; C07D 413/00; C07D 215/16; C07D 215/20

[52] U.S. Cl. ..... 514/212; 546/153; 546/156; 546/318; 546/123; 546/155; 544/279; 544/117; 544/58.6; 544/128; 544/127; 544/236; 544/350; 514/258; 514/250; 514/248; 514/300; 514/312; 514/228.2; 514/228.5; 514/234.2; 514/235.2; 514/234.5; 540/600; 540/597

[58] Field of Search ..... 546/153, 156, 318, 123, 546/155; 260/244.4, 243.3; 544/279, 117, 122, 58.6, 128, 127, 236, 350; 514/258, 222, 212, 239, 237, 236; 540/600, 597

[56] References Cited

U.S. PATENT DOCUMENTS 3,472,859 10/1969 Lesher ..... 546/153
3,673,184 6/1972 Minami et al. ..... 544/279

FOREIGN PATENT DOCUMENTS 0004279 2/1979 European Pat. Off. ..... 546/153

OTHER PUBLICATIONS

Shah et al., Quinolines Bulletin, Oct. 1984, pp. 1–6.
Shah et al., Quinolines Bulletin, Nov., 1985, vol. 1, pp. 1–6.

*Primary Examiner*—Mary C. Lee
*Assistant Examiner*—Robert C. Whittenbaugh
*Attorney, Agent, or Firm*—Sprung Horn Kramer & Woods

[57] ABSTRACT

The invention provides 4-pyridone-3-carboxylic acids and derivatives thereof together with a method for their preparation. Also included in the invention are compositions containing said 4-pyridone-3-carboxylic acids and derivatives and the use of said compounds and compositions as antibacterial and/or antifungal agents or for animal growth promotion or improved feed utilization.

37 Claims, No Drawings

4-PYRIDONE-3-CARBOXYLIC ACIDS AND/OR DERIVATIVES THEREOF

Matter enclosed in heavy brackets [ ] appears in the original patent but forms no part of this reissue specification; matter printed in italics indicates the additions made by reissue.

The invention relates to a process for the preparation of 4-pyridone-3-carboxylic acids and/or derivatives thereof, to certain new 4-pyridone-3-carboxylic acids and/or derivatives thereof, and to their use as antibacterial agents and as feed additives.

The preparation of 1-ethyl-4-quinolone-3-carboxylic acid ethyl ester by reacting N-ethyl-aniline with ethoxymethylene-malonic acid diethyl ester and subsequent cyclisation of the product in the presence of a polyphosphoric acid ester at elevated temperature is described in J. Het. Chem. 12, 557 (1975).

According to the present invention we provide a process for the production of 4-pyridone-3-carboxylic acids and/or derivatives thereof, in which an enamine of the general formula

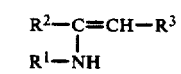

(I)

in which $R^1$ denotes alkyl, cycloalkyl, aralkyl, aryl or an amino group $—NR^4R^5$, in which $R^4$ and $R^5$ can be identical or different, and denote a straight-chain or branched $C_1$ to $C_4$ alkyl group or, together with the nitrogen atom which they substitute, and optionally a further hetero-atom, form a 5-membered to 7-membered ring, $R^2$ denotes a hydrogen atom, or an alkyl, aralkyl or aryl group and $R^3$ denotes a derivative (as hereinafter defined) of a carboxyl group, is reacted with an o-halogeno-(hetero-)aryl-carboxylic acid halide of the general formula

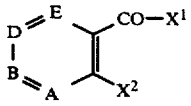

(II)

in which up to 3 of the symbols A, B, D and E denote a nitrogen atom and the symbols A, B, D and E remaining in each case denote an optionally substituted carbon atom, and $X^1$ and $X^2$ denote identical or different halogen atoms, in a first reaction stage at 0° to 80° C. in an anhydrous, aprotic solvent and in the presence of a base, and in a second reaction stage at 80° to 250° C. in the presence of a base, if appropriate the group $R^3$ is converted into the carboxyl group, and if appropriate this carboxyl group is converted into a salt thereof.

It is to be described as decidingly surprising that the enamines of the formula (I) are acylated on the carbon in the β-position relative to the nitrogen by the o-halogeno-(hetero-)aroyl halides of the formula (II) in the first reaction stage of the process according to the invention, whilst it is known from Chem. Ber. 50, 65 (1917) that benzoyl chlorides which are substituted in the ortho-position by bromine, nitro or acetoxy only react with acylation of the nitrogen. Furthermore, it is surprising that the intermediate products, of the formula (VI), from the first reaction stage of the process according to the invention react further in an unambiguous manner to give the end product of the formula (VII) according to the invention, in spite of the cis/trans isomerism made possible by the double bond.

The advantage of the process according to the invention is that only single compounds are formed in a so-called one-pot reaction which is simple to carry out.

It is, of course, possible to prepare the free carboxylic acids, and subsequently the salts of carboxylic acids, preferably the pharmaceutically usable salts, for example the alkali metal salts or alkaline earth metal salts, from the 4-pyridone-3-carboxylic acid derivatives of the invention, by suitable acid or alkaline saponification methods. Thus in the present application the term "derivative" in respect of a carboxylic acid means a derivative thereof which may be converted by the acid by an acid or alkaline saponification method. Preferred alkyl radicals $R^1$ and $R^2$ are saturated or unsaturated, straight-chain or branched alkyl radicals with 1 to 6 carbon atoms, for example methyl, ethyl, propyl, isopropyl, butyl, isobutyl, tert.-butyl, pentyl, hexyl, propenyl, butenyl, pentenyl or hexenyl. Preferred aliphatic radicals $R^1$ and $R^2$ are those with 1 to 4 carbon atoms, for example methyl, ethyl, propyl, isopropyl, butyl, isobutyl or tert.-butyl.

Particularly preferred aliphatic radicals $R^1$ are ethyl or tert.-butyl.

Preferred cycloalkyl radical $R^1$ are saturated or unsaturated carbocyclic ring systems with 3 to 7 carbon atoms which are optionally substituted by methyl or ethyl groups, for example cyclopropyl, cyclopropenyl, cyclobutyl, cyclobutenyl, cyclopentyl, cyclopentenyl, cyclohexyl, cyclohexenyl, cycloheptyl or cycloheptenyl. The cyclopropyl radical and the cyclohexyl radical may be mentioned as preferred cycloaliphatic radicals $R^1$.

Aralkyl radicals $R^1$ and $R^2$ which may be mentioned as preferred radicals are radicals with 1 to 4 carbon atoms in the aliphatic part and 6 to 10 carbon atoms in the aromatic part, for example benzyl, β-phenylethyl, naphthylmethyl or β-naphthylethyl. The benzyl radical is particularly preferred.

Aryl radicals $R^1$ and $R^2$ which may be mentioned as preferred radicals are aromatic, carbocyclic ring systems with 6 to 10 carbon atoms, for example phenyl, naphthyl, o-biphenyl, m-biphenyl or p-biphenyl. The phenyl radical is particularly preferred.

Preferred amino groups $R^1$ is the $—NR^4R^5$ grouping, in which $R^4$ and $R^5$ denote identical or different, straightchain or brnached $C_1$ to $C_4$ alkyl radicals which are for example methyl, ethyl, propyl, isopropyl, butyl or isobutyl, preferably methyl and ethyl and particularly preferably methyl.

The alkyl radicals $R^4$ and $R^5$, together with the nitrogen atom, of the amino group, which they substitute, and optionally a further hetero-atom, can also form a 5-membered to 7-membered heterocyclic ring. Possible optional further hetero-atoms are oxygen, sulphur or nitrogen, preferably oxygen or sulphur. Examples of such heterocyclic ring systems which may be mentioned are: pyrrolidine, piperidine, hexamethyleneimine, morpholine or thiomorpholine, preferably morpholine.

Preferred derivatives of the carboxyl group $R^3$ are the nitrile group, an ester group —$COOR^6$ or an acid amide group —CO—$NR^7R^8$, $R^6$, $R^7$ and $R^8$ denotes a $C_1$ to $C_4$ alkyl, preferably methyl or ethyl.

The radicals $R^7$ and $R^8$ also denote hydrogen. The radical $R^8$ can furthermore denote optionally substituted phenyl.

The symbols A, B, D and E together form a carbocyclic or heterocyclic aromatic ring fused onto the 5-position or 6-position of the pyridone ring. The heteroatoms can be up to 3 nitrogen atoms.

The symbols A to E mentioned can have, for example, the following meanings: all the symbols A to E are optionally substituted carbon atoms; A is a nitrogen atom and B, D and E are optionally substituted carbon atoms; D is a nitrogen atom and A, B and E are optionally substituted carbon atoms; A and B are nitrogen atoms and D and E are optionally substituted carbon atoms; A and D are nitrogen atoms and B and E are optionally substituted carbon atoms; A and E are nitrogen atoms and B and D are optionally substituted carbonatoms; A, B and E are nitrogen atoms and D is an optionally substituted carbon atom; and A, D and E are nitrogen atoms and B is an optionally substituted carbon atom.

Optionally, substituted carbon atoms can be the grouping —C—$R^9$, wherein $R^9$ can be identical or different in the case of individual carbon atoms and can have, for example, the following meaning: hydrogen, $C_1$ to $C_6$ alkyl, $C_1$ to $C_4$ alkoxy, $C_1$ to $C_6$ alkylmercapto, trifluoromethyl, halogen, cyano, carboxyl which is esterified by $C_1$ to $C_4$ alkyl, benzyl or phenyl which can each be substituted by $C_1$ to $C_3$ alkyl, nitro or halogen, or amino substituted by carbalkoxy. Examples of halogen which may be mentioned are: fluorine, chlorine, bromine and iodine, preferably chlorine or bromine.

Two of the radicals $R^9$ which are on two adjacent carbon atoms, for example on A and B or on B and D or on D and E, can represent, together with the two adjacent carbon atoms, a further fused-on benzene nucleus.

It is, of course, also possible for all the alkyl, cycloalkyl, aralkyl or aryl radicals $R^1$ to $R^8$ listed to be substituted by substituents which are inert under the reaction conditions of the process according to the invention. Examples of possible substituents are those mentioned in the definition of $R^9$.

Halogen radicals $X^1$ and $X^2$ are, for example, fluorine, chlorine, bromine or iodine, preferably chlorine or bromine and particularly preferably chlorine.

The process according to the invention is preferably carried out using an enamine of the general formula

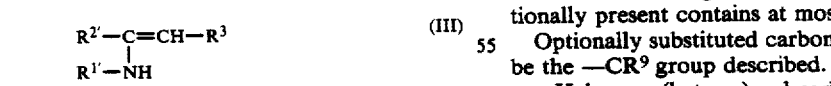

(III)

in which $R^{1'}$ denotes a tert.-alkyl, a $C_3$ to $C_7$ cycloalkyl, or a dialkylamino group —$NR^{4'}R^{5'}$, in which $R^{4'}$ and $R^{5'}$ denote a $C_1$ to $C_2$ alkyl group, or together complete a morpholinyl radical, $R^{2'}$ denotes a hydrogen atom, a $C_1$ to $C_4$ alkyl group or an optionally substituted benzyl or phenyl radical and $R^3$ has the above-mentioned meaning.

The process according to the invention is particularly preferably carried out using an enamine of the general formula

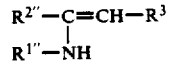

(IV)

in which $R^{1''}$ denotes a tert.-butyl, cyclopropyl, cyclohexyl or dimethylamino group or a N-morpholinyl radical.

$R^{2''}$ denotes a hydrogen atom or a $C_1$ to $C_4$ alkyl group and $R^3$ has the above-mentioned meaning.

Enamines which can be employed in the process according to the invention can be prepared, for example, by reacting propiolic acid methyl ester with primary amines according to Chem. Ber. 99, 2526 (1966), or from N,N-di-substituted hydrazines with acetoacetic acid derivatives according to Chem. Ber. 108, 1659 (1975).

The following β-enamino-carboxylic acid derivatives and β-enhydroazino-carboxylic acid derivatives may be mentioned as examples: β-methylaminocrotonic acid methyl ester, β-ethylaminocrotonic acid methyl ester, β-ethylaminocrotonic acid ethyl ester, β-ethylaminocrotonic acid n-propyl ester, β-n-propylaminocrotonic acid methyl ester, β-cyclopentylaminocrotonic acid methyl ester, β-cyclohexylaminocrotonic acid ethyl ester, 3-(2,2-dimethylhydrazino)crotonic acid methyl ester, 3-(2,2-dimethylhydrazino)crotonic acid ethyl ester, β-morpholinyl-aminocrotonic acid methyl ester, β-piperidinylamino-crotonic acid ethyl ester, β-ethylamino-acrylic acid methyl ester, β-i-propylaminoacrylic acid methyl ester, β-cyclopropylamino-acrylic acid methyl ester, β-cyclohexylamino-acrylic acid ethyl ester, β-t-butylamino-acrylic acid methyl ester, β-morpholinylamino-acrylic acid ethyl ester, β-methylaminocrotonic acid anilide, β-morpholinyl-amino-crotonic acid 4-chloroaniline, β-methylaminocrotonic acid nitrile, β-anilino-crotonic acid methyl ester, β-anilino-acrylic acid methyl ester, β-anilinoacrylic acid ethyl ester and β-(4-methoxyphenylamino)crotonic acid ethyl ester.

The process according to the invention is preferably carried out using those o-chloro-(hetero-)arylcarboxylic acid chlorides of the formula

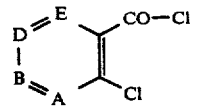

(V)

in which the symbols A, B, D and E have the above-mentioned meaning, but the heterocyclic radical optionally present contains at most two nitrogen atoms.

Optionally substituted carbon atoms can in each case be the —$CR^9$ group described.

o-Halogeno-(hetero-)aryl-carboxylic acid halides which can be employed in the process according to the invention, and processes for their preparation, are known. Thus, for example, J. Am. Chem. Soc. 40,233 (1908) describes the preparation of 2-ethylmercapto-6-chloropyrimidine-5-carboxylic acid chloride by reacting 2-ethylmercapto-4-oxo-3,4-dihydropyrimidine-5-carboxylic acid with phosphorus oxychloride. The reaction of 2-hydroxy-quinoxaline-3-carboxylic acid with thionyl chloride in the presence of a catalytic amount of dimethylformamide to give 2-chloroquinoxaline-3-carboxylic acid chloride is described in Arch. Pharm. 306, 401 (1973). The reaction 4-chloronicotinic acid with thionyl chloride under reflex to give 4-chloronicotinic acid chloride is described in J. Chem. Soc. (C), 1966, 1816.

Examples which may be mentioned of o-halogeno(-hetero-)aryl-carboxylic acid halides which can be employed in the process according to the invention are: 2-chloro-5-nitro-benzoyl chloride, 2-chloro-5-nitro-benzoyl bromide, 2-chloro-3-nitro-benzoyl chloride, 2-chloro-3-nitro-5-trifluoromethyl-benzoyl chloride, 2,4-dichloro-3-nitro-benzoyl chloride, 2,4-dichloro-5-nitro-benzoyl chloride, 2,4-dichloro-3,5-dinitro-benzoyl chloride, 2,6-dichloro-3,5-dinitro-benzoyl chloride, 2-chloro-3,5-dinitro-benzoyl chloride, 2-chloro-3,5-dinitro-benzoyl bromide, 2,4,5-trichloro-3-nitro-benzoyl chloride, 2,4,6-trichloro-3,5-dinitro-benzoyl chloride, 2-fluoro-5-nitro-benzoyl chloride, 2-chloro-nicotinic acid chloride, 2-chloro-4-methyl-nicotinic acid chloride, 2-chloro-6-methyl-nicotinic acid chloride, 4-chloro-nicotinic acid chloride, 2,6-dichloro-nicotinic acid chloride, 2,5,6-trichloro-nicotinic acid chloride, 2-bromonicotinic acid chloride, 2,5-dichloro-nicotinic acid choride, 2-chloro-5-nitro-nicotinic acid chloride, 2-chloro-4,6-dimethyl-5-nitro-nicotinic acid chloride, 2-methylmercapto-4-chloro-pyrimidine-5-carboxylic acid chloride, 2-ethylmercapto-4-chloro-pyrimidine-5-carboxylic acid chloride, 4-chloro-6-methoxy-pyrimidine-5-carboxylic acid chloride, 4-chloro-6-phenyl-pyrimidine-5-carboxylic acid chloride, 2,4-dichloro-pyrimidine-5-carboxylic acid chloride, 3-chloro-pyridazine-4-carboxylic acid chloride, 2,6-dichloro-pyridazine-4-carboxylic acid chloride, 2-chloro-pyrazine-3-carboxylic acid chloride and 2-chloro-quinoxaline-3-carboxylic acid chloride.

The first reaction stage of the process according to the invention is carried out in the temperature range from 0° to 80° C. and the second reaction stage is carried out in the temperature range from 80° to 250° C. Preferably, the first reaction stage is carried out from 10° to 60° C. and the second reaction stage from 100° to 150° C. The process according to the invention is carried out in an anhydrous, aprotic solvent or in a mixture of such solvents. Such a solvent can belong, for example, to the group comprising hydrocarbons, such as, for example, ligroin, cyclohexane, benzene or toluene, the group comprising chlorinated hydrocarbons, such as, for example, methylene chloride, chloroform, carbon tetrachloride, chlorobenzene or o-dichlorobenzene, the group comprising nitriles, such as, for example, acetonitrile, or the group comprising ethers, such as, for example, diethyl ether, tetrahydrofurane or dioxane. Dioxane is preferably employed as the solvent.

The solvents, from the list of examples, which have boiling points above about 80° C. can also be further used directly for the second reaction stage. Both reaction stages can be carried out in a so-called one-pot reaction in the case of this process variant.

In another process variant, after carrying out the first reaction stage, the low-boiling solvent is distilled off and replaced by a higher-boiling solvent. In this case, in addition to the examples of higher-boiling solvents listed, other solvents can also be used, for example dimethylformamide, dimethylsulphoxide, N-methylpyrrolidone, sulpholane or hexamethylphosphoric acid triamide.

In another process variant, the further reaction can be carried out with the low-boiling solvent from the first reaction stage if the second reaction stage is carried out under pressure. However, the process according to the invention is usually carried out under normal pressure.

Both reaction stages of the process according to the invention are carried out in the presence of bases. Bases which may be mentioned for the first reaction stage of the process according to the invention are tertiary organic amines, for example pyridine, triethylamine, N-methylmorpholine, N-methylpiperidine, quinoline or triethylenediamine. The first reaction stage is preferably carried out in the presence of pyridine or especially triethylamine.

The second reaction stage of the process according to the invention is carried out in the presence of a base, such as an amine, quaternary ammonium hydroxide, an alkali or alkaline earth hydroxide, bicarbonate, carbonate, etc. which is additionally added. Examples of possible bases for this purposes are: 1,5-diazabicyclo-[4.3.0]-non-5-ene (DBN), 1,8-diazabicyclo-[5.4.0]-undec-7-ene (DBU), triethylenediamine, triethylamine, potassium hydroxide, sodium hydroxide, sodium methylate, sodium ethylate, sodium hydride, butyl-lithium, lithium-phenyl or phenyl-magnesium bromide. 1,8-Diazabicyclo-[5.4.0]-undec-7-ene (DBU) is preferably employed for the second reaction stage.

The starting compounds of the formula (I) and (II) for the process according to the invention and the base in the first reaction step are generally employed in equimolar amounts relative to one another. In the second reaction stage, a further equimolar amount of base is added. It can be advantageous to employ an excess of base of 10 mol %.

The process according to the invention can be represented by the equations which follow, using the reaction of 2-ethylmercapto-4-chloro-pyrimidine-5-carboxylic acid chloride with β-methylamino-crotonic acid ethyl ester as an example:

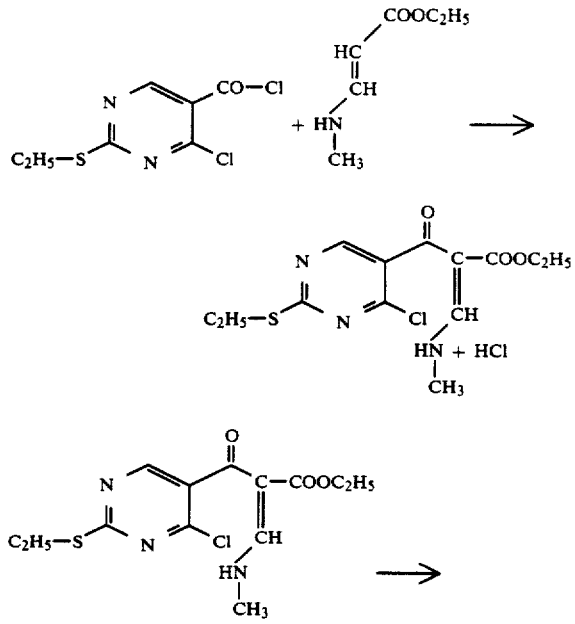

-continued

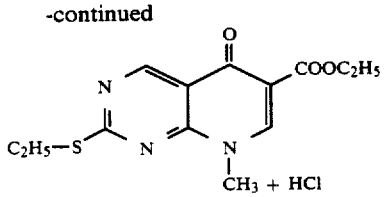

The process according to the invention can be carried out, for example, as follows:

(a) The enamine of the formula (I) and the tertiary amine from the group of bases for the first reaction stage are added successively to a solution of the o-halogeno-(hetero-)aroyl halide of the formula (II) in an anhydrous, aprotic solvent. After the reaction has ended, the solvent is distilled off. For working up, the reaction mixture of a water-insoluble solvent, such as, for example, methylene chloride or chloroform, and water and washed. The intermediate product of the formula (VI)

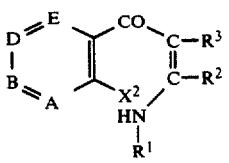

(VI)

which can be purified by recrystallisation, is obtained from the organic phase by distilling off the solvent. The reaction product of the formula (VI) from the first reaction stage is then further reacted, in an anhydrous, aprotic solvent with a boiling point above 80° C., with an equimolar amount of a base from the group for the second reaction stage. Working up is carried out analogously to that after the first reaction stage. For purification, for example, the product can be recrystallised from ethanol, acetonitrile or ethyl acetate.

(b) The sequence of the addition of the starting materials for the first reaction stage can be changed. Thus, the sequence can be, for example: 1. enamine, 2- o-halogeno-(hetero-)aroyl halide, and 3. the base.

Furthermore, the sequence of addition can be, for example: 1. enamine and base together, and 2. the o-halogeno-(hetero-)aroyl halide.

(c) It is, of course, possible to employ directly in the second reaction stage of the process according to the invention intermediate products of the formula (VI) which have been obtained, for example, by another route.

(d) If an anhydrous, aprotic solvent with a boiling point above 80° C. is used for the first reaction stage, both reaction stages of the process according to the invention can be carried out successively in one apparatus in a so-called one-pot reaction without separate isolation of the intermediate product of the formula (VI). Before increasing the reaction temperature for the second reaction stage, a base from the group of those suitable for the second reaction stage is merely added. Since the bases mentioned above for the second reaction stage, for example DBU, are frequently stronger than the bases which have been mentioned above for the first reaction stage, it is often necessary, when carrying out the one-pot process, to employ twice the molar amount of base for the second reaction stage, since half of this amount is necesary to liberate the weaker base of the first reaction stage.

The invention furthermore relates to new compounds which are 4-pyridone-3-carboxylic acids, and/or derivatives thereof, of the formula (VII)

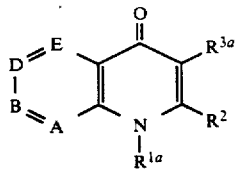

(VII)

or a salt thereof in which $R^{1a}$ denotes tert.-alkyl, cycloalkyl or an amino group $-NR^4R^5$, $R^{3a}$ denotes the carboxyl group or a derivative thereof (as hereinbefore defined) and $R^2$, $R^4$, $R^5$, A, B, D and E have the meanings indicated above.

The invention particularly relates to new 4-pyridone-3-carboxylic acids, and/or derivatives thereof, of the formula (VIII)

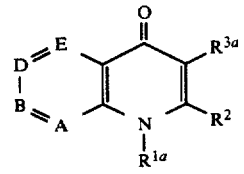

(VIII)

in which $R^{3a}$, $R^{1a}$, $R^2$, A, B, D and E have the abovementioned meaning, but the heterocyclic radical optionally present contains at most two nitrogen atoms, and pharmaceutically usable salts thereof.

The invention very particularly relates to new 4-pyridone-3-carboxylic acids of the formula (IX)

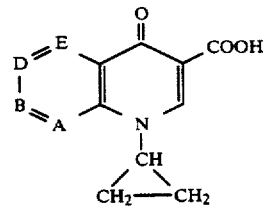

(IX)

in which A, B, D and E have the abovementioned meaning, and pharmaceutically usable salts thereof.

It has furthermore been found that new compounds according to the invention have outstanding antibacterial and fungicidal properties and moreover are active as growth regulators.

In particular, they have a bacteriostatic and bactericidal action, for example against Gram-negative bacteria, such as Escherichia, Proteus and Klebsiella. The improved antibacterial action of the new compounds according to the invention becomes particularly clear in the case of 1-cyclopropyl-7-methyl-1,8-naphthyrid-4-one-3-carboxylic acid (compound from Example 19), which, in comparison with 1-ethyl-7-methyl-1,8-naphthyrid-4-one-3-carboxylic acid, which is known ("nalidixic acid"; Ehrhart/ruschig, Arzneimittel (Medicaments) Volume 2: Chemotherapeutika (Chemotherapeutic Agents), Verlag Chemie 1968, page 1,568)

proved far superior in vitro and in vivo against Staphylococci, Escherichia coli, Proteus, Klebsiella, Pseudomonas and the like.

The improved antibacterial activity of the compounds according to the invention permits them to be used as active compounds in medicine, and they can be employed both for the prevention and for the treatment of systemic or local bacterial infections. Furthermore, the compounds according to the invention can also be used as feed additives for promoting growth and for improving feed utilisation in keeping animals, especially in keeping fatstock. In this case, the active compounds are preferably administered via the feed and/or drinking water.

The present invention furthermore relates to agents which contain the new compounds according to the invention. These include, for example, feedstuff concentrates, for keeping animals, which, in the customary manner, can also contain vitamins and/or mineral salts in addition to the active compounds, or pharmaceutical formulations.

The invention preferably relates to antibacterially active agents which contain compounds of the formula (VIII). The invention particularly preferably relates to those anti-bacterially active agents which contain the compounds of the formula (IX) or alkali metal salts or alkaline earth metal salts thereof.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingedient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portion suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solution and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. the coatings, envelopes and protective matrices may be made, for example, of polymeric substances or waxes.

The ingredient can also be made up in microencapsulated form together with one or several of the above-mentioned diluents.

The diulents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical composition which are ointments, pastes, creams and gels can, for example, contain the usual diluents, e.g. animal and vegetable fats, eaxes, paraffins, starch, tragacanth, cellulose derivatives, polyethylene glycols, silicones, bentonites, silicic acid, talc and zinc oxide or mixture of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvent having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solution and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium methahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generalll contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

The invention further relates to a medicated fodder comprising a compound of the present invention and a nutritious material.

The process, which belongs to the state of the art, for the preparation of 4-quinolone-3-carboxylic acid derivatives by reacting aromatic amines with alkoxymethylenemalonic acid diethyl ester gives reaction products which are single compounds only in the case of unsubstituted aromatic amines. Isomer mixtures are frequently obtained in the case of substituted aromatic amines (J. Het. Chem. 12, 557 (1975)).

The provision of new bactericides for combating bacteria which have become resistant towards known bactericides is an advance in the art.

The following Examples illustrate reactions of the present invention, some of which produce the novel compounds of the present invention.

EXAMPLE 1

33 g of β-methylaminocrotonic acid ethyl ester and 23.5 g of triethylamine are successively added dropwise to a solution of 43.9 g of 2-chloro-6-methyl-nicotinic acid chloride in 120 ml of absolute dioxane, whilst cooling with ice. The mixture is stirred at 25° C. for 2 hours, 72 g of 1,8-diazabicyclo-[5.4.0]undec-7-ene (DBU) are added dropwise and the mixture is heated under reflux for 5 hours. The solvent is then distilled off in vacuo and the residue is taken up in a chloroform/water mixture. The chloroform phase is dried over sodium sulphate and the chloroform is distilled off in vacuo. By recrystallisation of the residue from toluene/cyclohexane, 32.6 g (54% of the theoretical yield) of 1,27-trimethyl-4-oxo-1,8-naphthyridine-3-carboxylic acid ethyl ester of melting point 122° to 123° C. are obtained..

Saponification of the ester:

26 of 1,2,7-trimethyl-4-oxo-1,8-naphthyridine-3-carboxylic acid ethyl ester are heated to the boil under reflux with a solution of 6.2 g of potassium hydroxide in 100 ml of water and 100 ml of ethanol for about 4 hours. The ethyl alcohol is distilled off in vacuo, the aqueous solution is filtered, further water being added if appropriate, and the filtrate is acidified down to a pH value of 1 to 2 with 10% strength hydrochloric acid, whilst cooling with ice. The precipitate which forms is filtered off, washed with water and dried in vacuo at about 60° to 80° C. The resulting free carboxylic acid can be recrystallised from ethyl alcohol.

Yield: 9 g; melting point: 224° C.

EXAMPLES 2 TO 18

The esters and carboxylic acids of Examples 2 to 18 were obtained by a procedure analogous to that in Example 1. They are summarised in Table 1. The labelling of the radicals A, B, D, E, $R^1$, $R^2$ and $R^3$ relates to formulae (I) and (II) in the description.

TABLE 1

| Example No. | A | B | D | E | $R^1$ | $R^2$ | $R^3$ | Melting point (°C.) (Ester) | Melting point (°C.) (Acid) |
|---|---|---|---|---|---|---|---|---|---|
| 2 | CH | CH | C—$NO_2$ | CH | 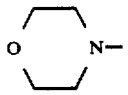 | $CH_3$ | —$COOC_2H_5$ | 211 | 210 (D)+ |
| 3 | CH | CH | C—$NO_2$ | CH | $CH_3$ | $CH_3$ | —$COOC_2H_5$ | 228 | 290 (D) |
| 4 | CH | CH | C—$NO_2$ | CH | $(CH_3)_2N$— | $CH_3$ | —$COOCH_3$ | 203 | 277 (D) |
| 5 | CH | C—Cl | C—$NO_2$ | CH | $(CH_3)_2N$— | $CH_3$ | —$COOCH_3$ | 193 | — |
| 6 | C—$NO_2$ | CH | CH | CH | $CH_3$ | $CH_3$ | —$COOCH_3$ | 238 | 285 (D) |
| 7 | CH | CH | C—$NO_2$ | CH | $CH_3$ | $CH_3$ | —CN | 216 | — |
| 8 | N | C—$SC_2H_5$ | N | CH | 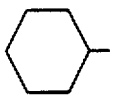 | H | —$COOCH_3$ | 147 | 229 (D) |

TABLE 1-continued

| Example No. | A | B | D | E | $R^1$ | $R^2$ | $R^3$ | Melting point (°C.) (Ester) | Melting point (°C.) (Acid) |
|---|---|---|---|---|---|---|---|---|---|
| 9 | CH | CH | C—$NO_2$ | CH | $C_2H_5$ | $CH_3$ | —$COOCH_3$ | 205 | 242 (D) |
| 10 | CH | CH | C—$NO_2$ | CH | 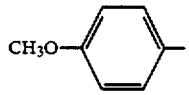 | $CH_3$ | $COOC_2H_5$ | 212 | 317 (D) |
| 11 | CH | CH | C—$NO_2$ | CH | 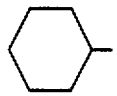 | $CH_3$ | $COOCH_3$ | 211 | — |
| 12 | N | C—$CH_3$ | CH | CH | —$(CH_2)_2N$—CO(H)$CH_3$ | $CH_3$ | $COOCH_3$ | 204 | 285 (D) |
| 13 | N | C—$CH_3$ | CH | CH | $CH_3$ | $CH_3$ | $COOCH_3$ | 162 | 230 (D) |
| 14 | CH | CH | C—$NO_2$ | CH | 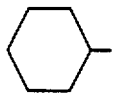 | $CH_3$ | $COOC_2H_5$ | 210 | 204 |
| 15 | N | C—$CH_3$ | CH | CH | $C_2H_5$ | $CH_3$ | $COOCH_3$ | 160 | 226 (D) |
| 16 | N | C—$SC_2H_5$ | N | CH | $CH_3$ | $CH_3$ | $COOCH_3$ | 184 | 252 (D) |
| 17 | CH | C—$SC_4H_9$—n | C—$NO_2$ | CH | $(CH_3)_2$—N | $CH_3$ | $COOCH_3$ | 204 | 184 |
| 18 | CH | CH | C—$NO_2$ | CH | $C_6H_5$ | $CH_3$ | $COOC_2H_5$ | 220 | — |
| 19 | N | CH | CH | CH | 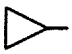 | H | $COOCH_3$ | 190–192 | |
| 20 | N | C—$CH(CH_3)_2$ | CH | CH | 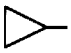 | H | $COOCH_3$ | 181–186 | |

+(D) means melting point with (partial) decomposition

EXAMPLE 21

First 14.1 g of β-cyclopropylaminoacrylic acid methyl ester and then 10.4 g of triethylamine are added dropwise to a solution of 19 g of 2-chloro-6-methylnicotinic acid chloride in 70 ml of absolute dioxane, whilst cooling with ice and stirring. The mixture is stirred at room temperature for 4 hours and at 40° C. for 0.5 hour, 31 g of 1,8-diazabicyclo-[5.4.0]-undec-7-ene (DBU) are added, whilst cooling with ice, and the mixture is heated under reflux for 6 hours. The solvent is then distilled off in vacuo and the residue is taken up in a chloroform/water mixture. The chloroform phase is dried with sodium sulphate and the chloroform is distilled off. After crystallising the residue from acetonitrile, 8.5 g of 1-cyclopropyl-7-methyl-4-oxo-1,8-naphthyridine-3-carboxylic acid methyl ester of melting point 204° to 205° C. are obtained. The corresponding carboxylic acid, obtained by saponification analogously to Example 1, melts at 229° to 230° C. (with decomposition).

EXAMPLE 22

33.8 g of β-cyclopenylaminoacrylic acid methyl ester in 20 ml of dioxane are added dropwise to a solution of 38 g of 2-chloro-6-methyl-nicotinic acid chloride in 120 ml of absolute dioxane, whilst cooling with ice and stirring, and 20.4 g of triethylamine are then added dropwise, a temperature of 10° to 15° C. being maintained. The mixture is then stirred at room temperature for 4 hours and at about 40° C. for 0.5 hour and, after cooling to 20° C., 63 g of DBU are added and the mixture is heated under reflux for 7 hours. The dioxane is then distilled off in vacuo, the residue is taken up in chloroform and the chloroform phase is washed with water. After the chloroform has been distilled off, the crude ester is heated under reflux directly with 80 ml of ethyl alcohol and a solution of 17 g of potassium hydroxide in 80 ml of water for 4 hours. The ethyl alcohol is distilled off in vacuo, the potassium salt of the carboxylic acid formed is dissolved in water, the solution is filtered and the carboxylic acid is precipitated from the filtrate with 10% strength hydrochloric acid, whilst cooling with ice. The precipitate, which has been filtered off and dried, is recrystallised from ethyl alcohol. 38.5 g of 1-cyclopentyl-7-methyl-4-oxo-1,8-naphthyridine-3-carboxylic acid of melting point 236° to 237° C. (with decomposition) are obtained.

EXAMPLES 23 to 31

The procedure followed in Examples 23 to 31 is analogous to that indicated in Example 22. The results are summarised in Table 2. As in the case of Table 1, the symbols A to $R^3$ relate to the formulae (I) and (II).

TABLE 2

| Example No. | A | B | D | E | $R^1$ | $R^2$ | $R^1$ saponified to | Melting point (°C.) |
|---|---|---|---|---|---|---|---|---|
| 23 | N | C—$CH_3$ | CH | CH | 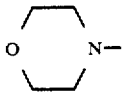 | $CH_3$ | COOH | 295 (D)+ |
| 24 | N | C—$CH_3$ | CH | CH | 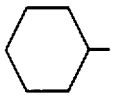 | H | COOH | 272 (D) |
| 25 | N | C—$CH_3$ | CH | CH | $(CH_3)_3C$— | H | COOH | 291 (D) |
| 26 | N | C—$CH_3$ | CH | CH | H<br>—$(CH_2)_2N$—$COOC_2H_5$ | H | COOH | 199 (D) |
| 27 | N | C—$CH_3$ | CH | CH | 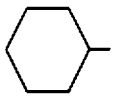 | $CH_3$ | COOH | 213 (D) |
| 28 | N | C—$CH_3$ | CH | CH | n-$C_3H_5$— | H | COOH | 208 (D) |
| 29 | N | C—$CH_3$ | CH | CH | $C_2H_5$ | H | COOH | 227 (D) |
| 30 | N | C—$CH_3$ | CH | CH | $CH_3$ | $CH_3$ | COOH | 230 (D) |
| 31 | N | C—$SC_2H_5$ | N | CH | 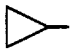 | H | COOH | 215 (D) |
| 32 | N | C—$SCH_3$ | N | CH | 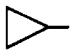 | H | COOH | 250 (D) |

+(D) means melting point with (partial) decomposition

EXAMPLE 33

77.5 g of β-morpholinylamino-crotonic acid anilide are added in portions to 65.4 g of 2-chloro-5-nitro-benzoyl chloride in 250 ml of absolute dioxane, whilst cooling with ice and stirring, and 24 g of pyridine are then added dropwise. The mixture is stirred at room temperature for 4 hours and at 50° to 60° C. for 2 hours, the dioxane is distilled off in vacuo and the reaction mixture is taken up in water. The precipitate which has formed is filtered off and, after drying, is recrystallised from ethyl acetate/acetonitrile. The yellow crystals of α-(2-chloro-5-nitro-benzoyl)-β-morpholinyl-amino-crotonic acid anilide melt at 190° to 191° C. Yield: 48 g.

19.3 g of the anilide are heated under reflux in 100 ml of dioxane with 7 g of DBU for 6 hours. The dioxane is then distilled off in vacuo and the residue is taken up in water. The precipitate is filtered off and washed with water. After drying, it is recrystallised from dimethylformamide/ethanol and 14 g of 2-methyl-1-morpholinyl-6-nitro-4-quinolone-3-carboxylic acid anilide of melting point 276° C. (with decomposition) are obtained.

EXAMPLE 34

138 g of β-(2,2-dimethylhydrazino)-crotonic acid methyl ester are added dropwise to a solution of 191.1 g of 2-chloro-5-nitro-benzyol chloride in 500 ml of anhydrous dioxane, whilst cooling with ice and stirring. 88.2 g of triethylamine are then added dropwise at about 10° to 15° C. and the mixture is stirred at room temperature for one hour and at 50° to 60° C. for 2.5 hours. The solvent is distilled off in vacuo and the residue is taken up in a chloroform/water mixture. The chloroform phase is dried over sodium sulphate. The chloroform is then distilled off in vacuo. After recrystallising the residue from ethyl acetate, 215.5 g of α-(2-chloro-5-nitro-benzoyl)-β-(2,2-dimethylhydrazino)-crotonic acid methyl ester are obtained. Melting point: 142° to 143° C.

A solution of 5.7 g of potassium hydroxide in 150 ml of ethyl alcohol is added to 34 g of the ester described. The mixture is then heated to 40° C. for 0.5 hour and under reflux for 4 hours. After working up as in the first reaction stage, 19.8 g of light yellow crystals of 1-dimethylamino-2-methyl-6-nitro-4-quinolone-3-carboxylic acid methyl ester are obtained. Melting point: 201° to 202° C.

EXAMPLE 35

A solution of 66 g of 2-chloro-5-nitro-benzoyl chloride in 30 ml of dioxane is added dropwise to a solution of 64.2 g of β-morpholinylamino-crotonic acid ethyl ester and 24 g of pyridine in 120 ml of absolute dioxane, whilst cooling with ice and stirring. The mixture is stirred at room temperature for one hour and at about 40° C. for one hour. It is worked up as in Example 33. After recrystallising the product from methanol, 82.3 g of α-(2-chloro-5-nitro-benzoyl)-β-morpholinylamino-crotonic acid ethyl ester are obtained. Melting point: 137° to 138° C.

(a) Cyclisation using DBU as the base 39.7 g of the acyclic ester described are heated under reflux in 100 ml of absolute dioxane with 16 g of DBU for 6 hours. The dioxane is distilled off in vacuo, the residue is worked up as in Example 33 and the product is recrystallised from ethanol, 16.5 g of 1-morpholinylamino-2-methyl-6-nitro-4-quinolone-3-carboxylic acid ethyl ester of melting point 210° to 211° C. are obtained.

(b) Cyclisation using sodium ethylate 26.5 g of the acyclic ester described above are added in portions to a solution of 1.54 g of metallic sodium in 150 ml of absolute ethanol, whilst cooling with ice and stirring, and the mixture is then heated under reflux for 4 hours. It is worked up as in Example 33 and the product is recrystallised from ethanol/acetonitrile, 18.6 g of 1-morpholinylamino-2-methyl-6-nitro-4-quinolone-3-carboxylic acid ethyl ester of melting point 209° to 210° C. are obtained.

(c) Cyclisation using potassium hydroxide/ethyl alcohol 26.5 g of the acyclic ester described above are rapidly added to 3.8 g of potassium hydroxide in 150 ml of ethanol. The mixture is heated under flux for 4 hours and worked up as described above. After recystallising the product from ethyl alcohol/acetonitrile, 22 g of the 4-quinolone ester already described under (a) and (b), of melting point 209° to 211° C., are obtained. The 1-morpholinylamino-2-methyl-6-nitro-4-quinolone-3-carboxylic acid obtainable by saponification melts at 265° C. (with decomposition).

Among the new 4-pyridone-3-carboxylic acid salts of the invention, those salts that are pharmaceutically acceptable are particularly important and are preferred. A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g., a metal hydroxide, ammonina or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenbenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the base obtained; the bases are converted into salts, the salts are separated and the base are liberated from the salts. In view of the close relationship between the free compounds and the compounds in the form of their salts, whenever a compound is referred to in this context, a corresponding salt is also intended, provided such is possible or appropriate under the circumstances.

The new free 4-pyridone-3-carboxylic acids of the general formula (VII) and their salts can be interconverted in any suitable manner; methods for such interconversion are known in the art.

The present invention also comprises pharmaceutically acceptable bioprecursors of the active compounds of the present invention.

For the purposes of this Sepcification the term "pharmaceutically acceptable bioprecursor" of an active compound of the invention means a compound having a structural formula different from the active compound but which nonetheless, upon administration to a warm-blooded animal is converted in the animal's body to the active compound.

It will be understood that the specification examples are illustrative but not limitative of the present invention and that other embodiments within the spirit and scope of the invention will suggest themselves to those skilled in the art.

What is claimed is:

1. A compound of the formula

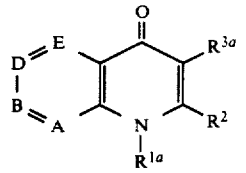

or a *pharmaceutically usable* salt thereof in which $R^{1a}$ denotes a cycloalkyl group having 3 to 7 carbon atoms or an amino group —$NR^4R^5$, in which $R^4$ and $R^5$ are identical or different, and denote a straight-chain or branched $C_1$ to $C_4$ alkyl group or, together with the nitrogen atom which they substitute, form a 5-membered to 7-membered ring, *said ring selected from the group consisting of pyrrolidine, piperidine, hexamethyleneimine, morpholine and thiomorpholine,*

$R^2$ denotes a hydrogen atom or an alkyl group having 1 to 6 carbon atoms, an aralkyl group having 1 to 4 carbon atoms in the aliphatic part and 6 to 10 carbon atoms in the aromatic part or an aryl group having 6 to 10 carbon atoms and $R^{3a}$ denotes a carboxyl group or a derivative which is a nitrile, an ester—*COOR*$^6$ or an acid amide —*CO—NR*$^7$*R*$^8$, *wherein* $R^6$, $R^7$ *and* $R^8$ *denote a* $C_1$–$C_4$ *alkyl,* the symbols A and D are nitrogen atoms and the symbols B and E remaining in each represent a carbon atom which is unsubstituted or substituted by $C_1$ to $C_6$ alkyl, $C_1$ to $C_4$ alkoxy, $C_1$ to $C_6$ alkylmercapto, trifluoromethyl, halogen, cyano, carboxyl which is esterified by $C_1$ to $C_4$ alkyl, benzyl or phenyl each of which is unsubstituted or substituted by $C_1$ to $C_3$ alkyl, nitro or halogen, or amino substituted by carbalkoxy.

2. A process for the production of a 4-pyridone-3-carboxylic acid or a derivative thereof which comprises reacting *an* enamine of the formula

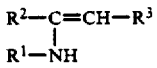

(I)

in which $R^1$ denotes an alkyl group having 1 to 6 carbon atoms, a cycloalkyl group having 3 to 7 carbon atoms, an aralkyl group having 1 to 4 carbon atoms in the aliphatic part and 6 to 10 carbon atoms in the aromatic part or an aryl group having 6 to 10 carbon atoms or an amino group —$NR^4R^5$, in which $R^4$ and $R^5$ are identical or different, and denote a straight-chain or branched $C_1$ to $C_4$ alkyl group or, together with the nitrogen atom which they substitute, form a 5-membered to 7-membered ring, $R^2$ denotes a hydrogen atom or an alkyl group having 1 to 6 carbon atoms, an aralkyl group having 1 to 4 carbon atoms in the aliphatic part and 6 to 10 carbon atoms in the aromatic part or an aryl group having 6 to 10 carbon atoms and $R^3$ denotes an ester or acid amide derivative of the carboxyl group, with [an o-halogeno-(hetero)-aryl-] *a* carboxylic acid halide of the formula

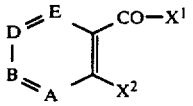

(II)

in which the symbols A and D are nitrogen atoms and the symbols B and E remaining in each case denote a carbon atom, and which is unsubstituted or substituted by $C_1$ to $C_6$ alkyl, $C_1$ to $C_4$ alkoxy, $C_1$ to $C_6$ alkylmercapto, trifluoromethyl, halogen, cyano, carboxyl which is esterified by $C_1$ to $C_4$ alkyl, benzyl or phenyl each of which is unsubstituted or substituted by $C_1$ to $C_3$ alkyl, nitro or halogen, or amino substituted by carbalkoxy *and wherein $X^1$ and $X^2$ denote identical or different halogen atoms.*

3. A medicated fodder comprising an amount of a compound as claimed in claim 1 effective for promoting growth and improving feed utilization and a nutritious material.

4. A process according to claim 2 in which the aprotic solvent is dioxane.

5. A process according to claim 2 in which the first reaction stage is carried out from 10° to 60° C. and the second reaction stage is carried out from 100° to 150° C. and the aprotic solvent is dioxane.

6. A process according to claim 2 in which R′ is cyclopropyl or cyclohexyl.

7. A process according to claim 2 in which the base in the first reaction stage is triethylamine and the base in the second reaction stage is 1,8-diazabicyclo-[5.4.0]-undec-7-ene.

8. A process according to claim 2 in which the enamine is of the formula

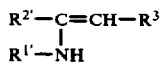

(III)

in which $R^{1'}$ denotes a tert.alkyl, a $C_3$, to $C_7$ cycloalkyl, or a dialkyl amino group —$NR^{4'}$—$R^{5'}$, in which $R^{4'}$ and $R^{5'}$ denote a $C_1$ or $C_2$ alkyl group or together complete a morpholinyl radical, $R^{2'}$ denotes a hydrogen atom or a $C_1$ to $C_4$ alkyl group or an optionally substituted benzyl or phenyl radical and $R^3$ has the same meaning as in claim 2.

9. A process according to claim 2 in which the enamine is of the formula (IV)

in which $R^{1''}$ denotes a tert.-butyl, cyclopropyl, cyclohexyl or dimethylamino group or a N-morpholinyl radical, $R^{2''}$ denotes a hydrogen atom or a $C_1$ to $C_4$ alkyl group and $R^3$ has the same meaning as in claim 2.

10. A process according to claim 2 in which the [o-halogeno-(hetero-)aryl-]carboxylic acid halide is a compound of the formula

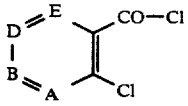

(V)

in which the symbols A, B, D and E have the same meaning as in claim 2, but the heterocyclic radical [optionally present] contains at most two nitrogen atoms.

11. A compound according to claim 1 in which $R^{1a}$ denotes a tert.-butyl, cyclopropyl, cyclohexyl, dimethylamino or N-morpholinyl radical.

12. A compound according to claim 1 of the formula

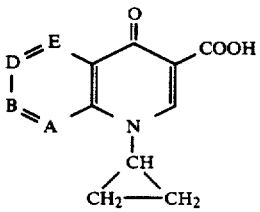

(IX)

in which A, B D and E have the same meanings as in claim 1.

13. A pharmaceutical composition containing as an active ingredient an antibacterially or antifungally effective amount of a compound according to claim 1 in admixture with a solid or liquefied gaseous diluent or in admixture with a liquid diluent other than a solvent of a molecular weight less than 200 except in the presence of a surface-active agent.

14. A pharmaceutical composition containing as an active ingredient as antibacterially or antifungally effective amount of a compound according to claim 1 in the form of a sterile or physiologically isotonic aqueous solution.

15. A comparison according to claim 13 containing from 0.5 to 95% by weight of the said active ingredient.

16. A medicament in dosage unit form comprising an antibacterially or antifungally effective amount of a compound according to claim 1 together with an inert pharmaceutical carrier.

17. A medicament of claim 16 in the form of tablets, pills, dragees, capsules, ampoules, or suppositories.

18. A method of combating bacterial diseases in warm-blooded animals which comprises administering to the said animals an effective amount of an active compound according to claim 1 either alone or in admixture with a diluent or in the form of a medicament.

*19. A compound of the formula*

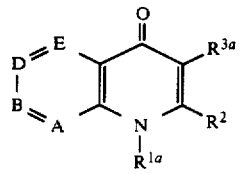

*or a pharmaceutically useable salt thereof in which*

*$R^{1a}$ denotes a cycloalkyl group having 3 to 7 carbon atoms or an amino group —$NR^4R^5$, in which*

*$R^4$ and $R^5$ are identical or different, and denote a straight-chain or branched $C_1$ to $C_4$ alkyl group or, together with the nitrogen atom which they substitute, form a 5-membered to 7-membered ring, said ring selected from the group consisting of pyrrolidine, piperidine, hexamethyleneimine, morpholine and thiomorpholine,*

*$R^2$ denotes a hydrogen atom or an alkyl group having 1 to 6 carbon atoms, an aralkyl group having 1 to 4 carbon atoms in the aliphatic part and 6 to 10 carbon atoms in the aromatic part or an aryl group having 6 to 10 carbon atoms and*

*$R^{3a}$ denotes a carboxyl group or a derivative which is a nitride, an ester—$COOR^6$ or an acid amide —CO—$NR^7R^8$, wherein $R^6$, $R^7$ and $R^8$ denote a $C_1$–$C_4$ alkyl, the symbols A, B, D and E at most represent two nitrogen atoms and the remaining symbols in each case represent a carbon atom which is unsubstituted or substituted by $C_1$ to $C_6$ alkyl, $C_1$ to $C_4$ alkoxy, $C_1$ to $C_6$ alkylmercapto, trifluoromethyl, halogen, cyano, carboxyl which is esterified by $C_1$ to $C_4$ alkyl, benzyl or phenyl said benzyl or phenyl being unsubstituted or substituted by $C_1$ to $C_3$ alkyl, nitro or halogen, or amino substituted by carbalkoxy.*

*20. A compound according to claim 19, wherein each of A, B, D and E is a carbon atom.*

*21. A compound according to claim 20 of the formula*

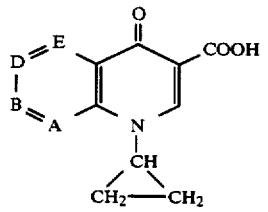

(IX)

*in which A, B, D and E have the same meanings as in claim 20.*

*22. A pharmaceutical composition containing as an active ingredient an antibacterially or antifungally effective amount of a compound according to claim 20 in admixture with a solid or liquefied gaseous diluent or in admixture with a liquid diluent other than a solvent of a molecular weight less than 200 except in the presence of a surface-active agent.*

*23. A pharmaceutical composition containing as an active ingredient an antibacterially or antifungally effective amount of a compound according to claim 20 in the form of a sterile or physiologically isotonic aqueous solution.*

*24. A composition according to claim 21 containing from 0.5 to 95% by weight of the said active ingredient.*

*25. A medicament in dosage unit form comprising an antibacterially or antifungally effective amount of a compound according to claim 20 together with an inert pharmaceutical carrier.*

*26. A medicament of claim 25 in the form of tablets, pills, dragees, capsules, ampoules, or suppositories.*

*27. A method of combating bacterial diseases in warm-blooded animal which comprises administering to the said animals an effective amount of an active compound according to claim 20 either alone or in admixture with a diluent or in the form of a medicament.*

*28. A medicated fodder comprising an amount of a compound as claimed in claim 20 effective for promoting growth and improving feed utilization and a nutritious material.*

*29. A process for the production of a 4-pyridone-3-carboxylic acid or a derivative thereof which comprises reacting an enamine of the formula*

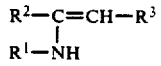

(I)

*in which*

*$R^1$ denotes an alkyl group having 1 to 6 carbon atoms, a cycloalkyl group having 3 to 7 carbon atoms, an aralkyl group having 1 to 4 carbon atoms in the aliphatic part and 6 to 10 carbon atoms in the aromatic part or an aryl group having 6 to 10 carbon atoms or an amino group —$NR^4R^5$,*

*in which*

*$R^4$ and $R^5$ can be identical or different, and denote a straight-chain or branched $C_1$ to $C_4$ alkyl group or, together with the nitrogen atom which they substitute, form a 5-membered to 7-membered ring, $R^2$ denotes a hydrogen atom or an alkyl group having 1 to 6 carbon atoms, an aralkyl group having 1 to 4 carbon atoms in the aliphatic part and 6 to 10 carbon atoms in the aromatic part or an aryl group having 6 to 10 carbon atoms and*

*$R^3$ denotes an ether or acid amide derivative of the carboxyl group, with an o-halogeno-(hetero)-aryl-carboxylic acid halide of the formula*

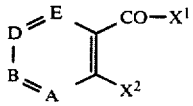

(II)

*in which*

*at most two of the symbols A, B, D and E are nitrogen atoms and the symbols remaining in each case denote a carbon atom, and which is unsubstituted or substituted by $C_1$ to $C_6$ alkyl, $C_1$ to $C_4$ alkoxy, $C_1$ to $C_6$ alkylmercapto, trifluoromethyl, halogen, cyano, carboxyl which is esterified by $C_1$ to $C_4$ alkyl, benzyl or phenyl each of which is unsubstituted or substituted by $C_1$ to $C_3$ alkyl, nitro or halogen, or amino substituted by carbalkoxy.*

*30. A process according to claim 29, wherein A, B, D and E each is a carbon atom.*

*31. A process according to claim 30 in which the aprotic solvent is dioxane.*

*32. A process according to claim 30 in which the first reaction stage is carried out from 10° to 60° C. and the second reaction stage is carried out from 100° to 150° C. and the aprotic solvent is dioxane.*

*33. A process according to claim 30 in which R' is cyclopropyl or cyclohexyl.*

*34. A process according to claim 30 in which the base in the first reaction stage is triethylamine and the base in the second reaction stage is 1,8-diazabicyclo-[5.4.0]-undec-7-ene.*

*35. A process according to claim 30 in which the enamine is of the formula*

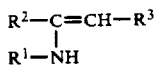

(III)

*in which*

*$R^1$ denotes a tert.alkyl, a $C_3$ to $C_7$ cycloalkyl, or a dialkyl amino group —$NR^4$—$R^5$,*

*in which*

*$R^4$ and $R^5$ denote a $C_1$ or $C_2$ alkyl group or together complete a morpholinyl radical,*

*$R^2$ denotes a hydrogen atom or a $C_1$ to $C_4$ alkyl group or an optionally substituted benzyl or phenyl radical and*

*$R^3$ denotes an ester or acid amide derivative of the carboxyl group, with a carboxylic acid halide of the formula*

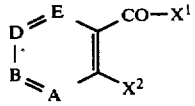

(II)

*in which*

*at most two of the symbols A, B, D and E are nitrogen atoms and the symbols remaining in each case denote a carbon atom, and which is unsubstituted or substituted by $C_1$ to $C_6$ alkyl, $C_1$ to $C_4$ alkoxy, $C_1$ to $C_6$ alkylmercapto, trifluoromethyl, halogen, cyano, carboxyl which is esterified by $C_1$ to $C_4$ alkyl, benzyl or phenyl each of which is unsubstituted or substituted by $C_1$ to $C_3$ alkyl, nitro or halogen, or amino substituted by carbalkoxy.*

*36. A process according to claim 30 in which the enamine is of the formula*

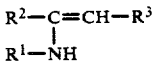

(IV)

*in which*

*$R^1$ denotes a tert.-butyl, cyclopropyl, cyclohexyl or dimethylamino group or a N-morpholinyl radical,*

*$R^2$ denotes a hydrogen atom or a $C_1$ to $C_4$ alkyl group and*

*$R^1$ denotes an alkyl group having 1 to 6 carbon atoms, a cycloalkyl group having 3 to 7 carbon atoms, an aralkyl group having 1 to 4 carbon atoms in the aliphatic part and 6 to 10 carbon atoms in the aromatic part or an aryl group having 6 to 10 carbon atoms or an amino group —$NR^4R^5$.*

*37. A process according to claim 30 in which the o-halogeno-aryl-carboxylic acid halide is a compound of the formula*

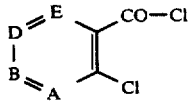

(v)

*in which the symbols A, B, D and E have the same meaning as in claim 30.*

* * * * *

UNITED STATES PATENT AND TRADEMARK OFFICE

CERTIFICATE OF CORRECTION

PATENT NO. : Re. 32,975

DATED : July 4, 1989

INVENTOR(S) : Klaus Grohe et al.

It is certified that error appears in the above-identified patent and that said Letters Patent is hereby corrected as shown below:

Col. 22, line 40 Delete "an o-halogeno-(hetero)-aryl-"

Signed and Sealed this

Fifteenth Day of November, 1994

*Attest:*

*Attesting Officer*

Bruce Lehman

BRUCE LEHMAN

*Commissioner of Patents and Trademarks*